United States Patent [19]
Ziegler et al.

[11] Patent Number: 5,726,343
[45] Date of Patent: Mar. 10, 1998

[54] PROCESS FOR THE PREPARATION OF ARYLACETIC ESTER DERIVATIVES VIA PALLADIUM-CATALYZED CROSS COUPLING REACTION

[75] Inventors: Hugo Ziegler, Witterswil; Denis Neff, Monthey; Wolfgang Stutz, Münchwilen, all of Switzerland

[73] Assignee: Novartis Corporation, Summit, N.J.

[21] Appl. No.: 676,364

[22] PCT Filed: Jan. 16, 1995

[86] PCT No.: PCT/EP95/00146

§ 371 Date: Jul. 22, 1996

§ 102(e) Date: Jul. 22, 1996

[87] PCT Pub. No.: WO95/20569

PCT Pub. Date: Aug. 3, 1995

[30] Foreign Application Priority Data

Jan. 27, 1994 [CH] Switzerland ............... 249/94-7

[51] Int. Cl.⁶ ............... C07D 213/53; C07C 251/48
[52] U.S. Cl. ............... 560/35; 558/286; 558/287; 544/319
[58] Field of Search ............... 558/286, 287; 562/19; 560/35

[56] References Cited

U.S. PATENT DOCUMENTS 4,999,042 3/1991 Anthony et al. ............... 71/88
5,157,144 10/1992 Anthony et al. ............... 560/35

FOREIGN PATENT DOCUMENTS

B633735 12/1991 Australia.
254426 1/1988 European Pat. Off..
A460575 12/1991 European Pat. Off..
2029223 3/1980 United Kingdom.

OTHER PUBLICATIONS

Chemical Abstracts, 55, 19839e (1961).
Chemical Abstracts, 55, 3484 b (1961).
Chemical Abstracts, 78, 58494 (1973).
Noria Miyaura et al, Tetrahedron Letters, Vol. 27, pp. 3745-3748 (1986).
M.J. Sharp et al., Tetrahedron Letters, Vol. 28, pp. 5093-5096 (1987).
Tatano Ishiyama et al., Chemistry Letters, Vol. pp. 25-28, (1987) The.

Primary Examiner—Zinna Northington Davis
Attorney, Agent, or Firm—Michael P. Morris; Edward McC. Roberts

[57] ABSTRACT

Process for the preparation of 2-methoxyimino-2-arylacetic esters of formula (I) in which R is $C_1$–$C_{12}$alkyl, which comprises reacting an appropriately substituted boronic acid of general formula (II) or the trimeric form (III) herein, which is in equilibrium with it, in the presence of a Pd catalyst, with a methoxyiminoacetic ester of formula (IV) in which R is $C_1$–$C_{12}$alkyl and X is a leaving group. According to a further process variant, in principle the groups which split off the two reactants may change places. The process can be applied not only to phenyl derivatives but also to larger ring systems (naphthyl, pyridyl, heterocycles).

18 Claims, No Drawings

PROCESS FOR THE PREPARATION OF ARYLACETIC ESTER DERIVATIVES VIA PALLADIUM-CATALYZED CROSS COUPLING REACTION

This application is a 371 of PCT/EP95/00146.

The present invention relates to a novel process for the preparation of an unsubstituted or ring-substituted 2-methoxyimino-2-arylacetic ester of the formula I

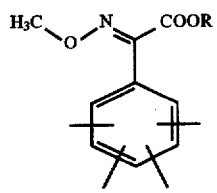

wherein one CH group of the aromatic ring group may be replaced by N forming pyridyl and wherein two of the four substitutable valencies of the ring may in adjacent position represent a fused-on, unsubstituted or substituted five- or six-membered ring which may contain one to three identical or different heteroatoms selected from N, S and O, and in which R is $C_1$–$C_{12}$alkyl, A) by reaction of boronic acid represented by the structural formula II

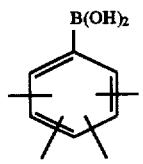

or of the trimeric form III

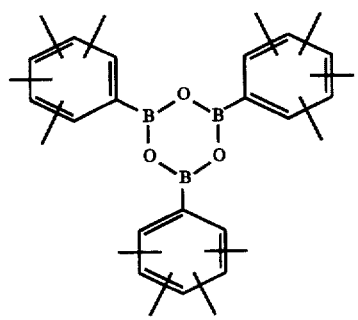

which is in equilibrium with it, in the presence of a palladium catalyst, with a methoxyiminoacetic ester of the general formula IV

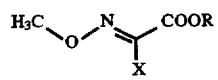

in which R is $C_1$–$C_{12}$alkyl and

X is a leaving group, or

B) by reaction of a methoxyiminoacetic ester of the formula Xa or Xb

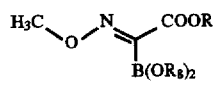

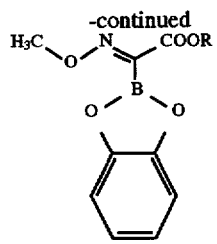

in which R and $R_8$ are each $C_1$–$C_{12}$alkyl
in the presence of a Pd catalyst, with a halophenyl compound of the general formula XI

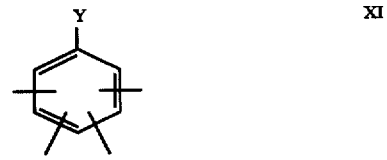

which is substituted as desired and in which

Y is Br or I and the four valencies in the phenyl ring represent the possible substituents mentioned for the structural formula I.

The term leaving group refers to a nucleofugic radical. Examples are, for instance, halogen (e.g. chlorine, bromine or iodine) or sulfonates [—O—$SO_2$alkyl($C_1$-$C_4$), —O—$SO_2$—$C_6H_5$, —O—$SO_2$—$C_6H_4$—$CH_3$, —O—$SO_2$—$CF_3$, etc.].

Particular preference is given to compounds of the formula IV, Xa and Xb in which R=$CH_3$.

The palladium catalyst can in principle be chosen as desired. Metallic Pd or Pd/C can be used. Preferred examples are the following compounds: $Pd^{(II)}(OAc)_2$, $(\varnothing_3P)_2Pd^{(II)}(OAc)_2$, $(\varnothing_3P)_2Pd^{(II)}Cl_2$, $(\varnothing_3P)_4Pd^{(O)}$, bis[1,2-bis(diphenylphosphino)ethane]palladium$^{(O)}$, dichloro[1,1'-bis(diphenylphosphino)ferrocene]palladium$^{(II)}$, dichloro[1,3-bis(diphenylphosphino)propane]Pd$^{(II)}$, dichloro[1,4-bis(diphenylphosphino)-butane]Pd$^{(II)}$, dichloro[1,2-bis(diphenylphosphino)ethane]Pd$^{(II)}$, dichlorobis(triphenylstet wherein $\varphi$ denotes phenyl. This list of Pd catalysts is not limiting.

More precisely, the invention relates to a process for the preparation of a microbicidally/insecticidally active compound of the formula Ia

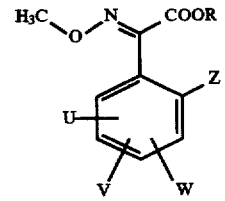

from boronic acid IIa represented by the structure

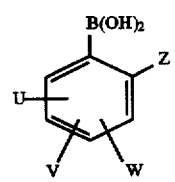

in which

R is $C_1$–$C_{12}$alkyl and

U, V, W and Z are as defined below:

Z is halogen, nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted heteroarylalkyl, unsubstituted or substituted heteroaryloxyalkyl, unsubstituted or substituted heteroarylthioalkyl, unsubstituted or substituted alkenyl, unsubstituted or substituted aralkenyl, unsubstituted or substituted aryloxyalkenyl, unsubstituted or substituted arylthioalkenyl, unsubstituted or substituted heteroarylalkenyl, unsubstituted or substituted heteroaryloxyalkenyl, unsubstituted or substituted heteroarylthioalkenyl, unsubstituted or substituted alkynyl, unsubstituted or substituted arylalkynyl, unsubstituted or substituted heteroarylalkynyl, unsubstituted or substituted aryl, unsubstituted or substituted heteroaryl, unsubstituted or substituted arylazo, unsubstituted or substituted acylamino, —$OR_{12}$, —$SR_{13}$, —$SOR_{14}$, —$SO_2R_{15}$, —$COOR_{16}$, —$CONR_{17}R_{18}$, —$COR_{19}$, —$CR_{20}=NR_{21}$, —$N=CR_{22}R_{23}$—, —$CR_{24}=N—OR_{25}$, —$CR_{25}R_{26}$—O—$N=CR_{27}R_{28}$, —$CH_2$—$OCOR_{39}$ or —$NR_{37}R_{38}$, in which the groups $R_{12}$ to $R_{28}$ and $R_{38}$ and $R_{39}$ are identical or different and are hydrogen, unsubstituted or substituted $C_1$-$C_6$alkyl, unsubstituted or substituted $C_1$-$C_6$alkenyl, unsubstituted or substituted $C_1$-$C_6$alkynyl, unsubstituted or substituted $C_3$-$C_6$cycloalkyl, unsubstituted or substituted cycloalkylalkyl, unsubstituted or substituted aryl, unsubstituted or substituted heteroaryl, unsubstituted or substituted aralkyl, unsubstituted or substituted heteroarylalkyl, unsubstituted or substituted aryloxyalkyl, unsubstituted or substituted arylthioalkyl or unsubstituted or substituted heteroarylthioalkyl and $R_{37}$ is hydrogen or $C_1$-$C_4$alkyl, and in which U, V and W are identical or different and are hydrogen or have one of the definitions specified for Z, or in which two of the groups Z, U, V and W in adjacent positions of the phenyl ting, together with the carbon atoms in these positions, form an unsubstituted or substituted five- or six-membered aromatic or cycloaliphatic ting which is fused onto the aryl ring and which may or may not contain one to three heteroatoms (N, S, O).

It is preferred to prepare compounds of the formula Ia in which

Z is —A—$R_1$ and

—A— adjacent to the aryl group is oxygen or is the group —C≡C—, —$CR_{30}=CR_{31}$—, —$CHR_{31}$—$CHR_{30}$—, —$CHR_{31}O$—, —$OCHR_{31}$, —CO—O—, —$CONR^{30}$—, —$CHR_{31}S$—, —$CR_{31}=N$—, —$CHR_{31}$—OCO—, —$CHR_{31}ON=CR_{30}$—, —$CR_{31}=N$—O—, —$N=CR_{30}$—, —N=N— or —$CHR_{30}$— and $R_1$ is unsubstituted or substituted alkyl, unsubstituted or substituted alkenyl, unsubstituted or substituted alkynyl, unsubstituted or substituted aralkyl, unsubstituted or substituted heteroarylalkyl, unsubstituted or substituted aryloxyalkyl, unsubstituted or substituted heteroaryloxyalkyl or heteroarylthioalkyl or unsubstituted or substituted aryl or unsubstituted or substituted heteroaryl, and $R_{30}$ and $R_{31}$ are identical or different and are straight-chain or branched $C_1$-$C_4$alkyl or hydrogen.

Particularly preferred compounds in the context of formula Ia which are prepared are those in which —A— is the group —O—, —$CH_2$—O—, —O—$CH_2$—, —$CN_2OH=CR_2$—, —$CH_2$—, —$CH_2$—$CH_2$—, —CH=CH— or —C≡C— and $R_1$ is unsubstituted or substituted aryl or unsubstituted or substituted heteroaryl, and $R_2$ is hydrogen, $C_1$-$C_4$alkyl, $C_3$-$C_6$cycloalkyl, $CF_3$, $C_1$-$C_4$alkoxy, $C_1$-$C_4$alkylthio or $C_1$-$C_4$alkoxy-$C_1$-$C_2$alkyl, or $R_1$ and $R_2$, together with the carbon atom to which they are attached, form an unsubstituted or substituted four- to seven-membered carbocyclic ring which may or may not contain an oxygen or sulfur atom and which may also have an unsubstituted or substituted fused-on benzene ring.

The reaction is carried out in an inert solvent or solvent mixture (e.g. a hydrocarbon such as hexane, benzene, toluene or, xylene, an ether such as diethyl ether, dimethoxyethane or tetrahydrofuran, a nitrile such as acetonitrile, an amide such as dimethylformamide, or a halogenated hydrocarbon such as carbon tetrachloride, etc.) in the presence of a base, for example alkali metal compounds or alkaline earth metal compounds such as the hydroxides, oxides or carbonates of lithium, sodium, potassium, magnesium, calcium and barium in their solid form or as aqueous solution, and also oxides such as ZnO, $Al_2O_3$, $Ag_2O$, etc., in their solid form or as aqueous solution. Examples of further bases are amines such as triethylamine, pyridine, piperidine and 4-dimethylaminopyridine.

The reaction temperatures are preferably in the range from 0° C. up to the boiling point of the solvent.

In many cases it is preferred to use $(Ø_3P)_4Pd^{(o)}$ as catalyst, to use toluene, dimethoxyethane, tetrahydrofuran or dimethylformamide as solvent, to use triethylamine, sodium hydroxide solution or potassium hydroxide solution, aqueous sodium carbonate or potassium carbonate or sodium hydrogen carbonate or potassium hydrogen carbonate as base, and to employ a reaction temperature of from 60° C. to the reflux temperature of the reaction mixture.

The novel synthesis according to the invention is distinguished by a simple procedure which leads in high yield to compounds of the formula I and/or Ia, which are obtained in highly pure form, and represents a considerable preparative advantage in relation to previously disclosed processes for obtaining compounds of the formula I.

As is evident, the effect of the other substituents on the aryl reactant II or XI is of minor significance in the course of the reaction. The critical factor is the ready tendency of the substituents —$B(OH)_2$ or —$B(OR_8)_2$ and —X or Y to split off from the particular reactant in the presence of Pd and/or a Pd salt.

The preparation of the compounds of the general formula II or, respectively, III is carried out by methods which are known per se (cf. R. Köster, in Houben-Weyl, Volume 13/3a, pp. 616–652). Compounds of the formula XI having a leaving group Y which can be split off readily are known from the literature and described in abundance.

Processes for the preparation of methoxyiminophenylacetic ester derivatives of the formula I are described in EP-A-253 123, EP-B-254 426, EP-299 694, EP-336 211, EP-354 571, EP-363 818, EP-A-525 516, EP-A460 575, EP-A463 488, EP-A-554 767 and further publications.

The methoximinoacetic esters of the general formula IV and of the formula X are novel and part of the invention.

They are prepared
a) by reacting a methoxy amide of the general formula V

with a halogenating agent such as phosphorus oxytrichloride, phosphorus oxytribromide, phosphorus pentachloride, phosphorus pentabromide, thionyl chloride, thionyl bromide, phosgene, triphenylphosphine/carbon tetrachloride, and triphenylphosphine/carbon tetrabromide.

Preferred reagents are phosphorus oxytrichloride and phosphorus oxytribromide.

The reaction can be carried out in an inert solvent such as, for example, toluene, dimethoxyethane, dimethylformamide, 1,2-dichloroethane, etc., in a temperature range between room point and the boiling temperature of the solvent. The halogenating agent is preferably used in excess as solvent, and the reaction temperature preferably chosen is its boiling point.

Otherwise, the preparation of the compounds of the formula IV is carried out in analogy to that of imino halides from amides (cf. Bonnett in Patai's "The Chemistry of the Carbon-Nitrogen Double Bond", pp. 597–662 (Interscience Publishers, New York, 1970)).

The compounds of the formula IV in which X is iodine are advantageously prepared by halogen exchange with sodium iodide in acetone or sodium iodide in an apolar solvent in the presence of a catalytic quantity of iron(III) chloride from the corresponding compounds of the formula IV in which X is chlorine or bromine (cf. Miller and Nunn; Tetrahedron Lett. 2691 (1974)). The preparation of the compounds of the formula IV in which X is a sulfonyl radical is carried out by reaction of a compound V with a corresponding sulfonyl halide. The compounds of the formula IV can also be prepared b) by reacting a methoxyiminoacetic ester of the general formula VI

with a halogenating agent such as, for example, chlorine or bromine.

The reaction is carried out in a diluent (e.g. water, alcohol, ether, (halogenated) hydrocarbon, etc.) in the temperature range from 0° C. to the boiling point of the diluent, preferably at from 0° C. to 30° C. The compounds of the formula V are already known (EP 465 986) or can be obtained by already known methods.

Sulfonates as leaving group Y in compounds of the formula XI can be obtained by reaction of the corresponding phenol (Y=OH) with a sulfonyl halide, especially sulfonyl chloride, and especially when activating groups are present in the phenyl ring.

The compounds of the formula VI are either already known (DE 3 405 327 (1985)) or can be prepared analogously.

The novel process according to the invention is furthermore distinguished by a) the use of boronic acid derivatives, for example arylboronic acid derivatives, as components which are simple and are readily accessible, and also by b) the ready accessibility (high yields!) of α-bromo-o-tolueneboronic acid (Torssell, Ark. Kemi 10, 507, 509 (1957); Snyder et al., J. Am. Chem. Soc. 80, 835 and 3611 (1958)), which may be used as intermediate for the preparation of the compounds of the general formula IIa in which Z is, for example, substituted alkyl, unsubstituted or substituted aryloxyalkyl, unsubstituted or substituted arylthioalkyl, unsubstituted or substituted heteroaryloxyalkyl, unsubstituted or substituted heteroarylthioalkyl, $-CR_{25}R_{26}-ON=CR_{27}R_{28}$ or $-CH_2OCOR_{39}$, and U, V and W are as defined above.

PREPARATION EXAMPLES

Example 1

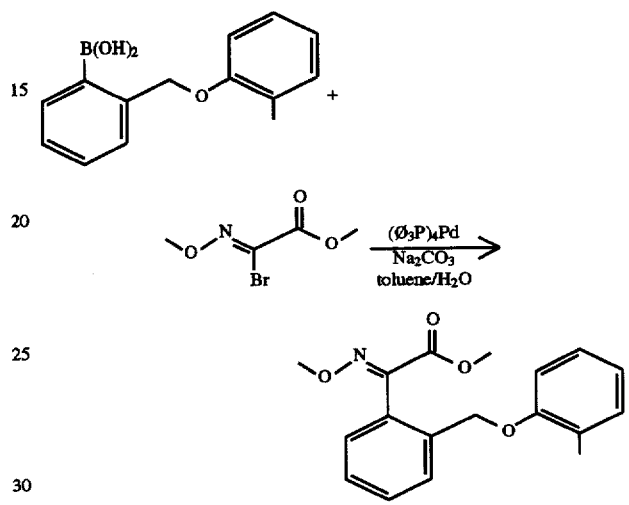

A mixture of 0.8 g of 2-(o-tolyloxymethyl) benzeneboronic acid, 0.8 g of methyl bromomethoxyiminoacetate, 0.38 g of tetrakis (triphenylphosphine)palladium, 5 ml of a 1-molar sodium carbonate solution and 15 ml of toluene is maintained at reflux with vigorous stirring under an inert gas atmosphere for 6 hours. After the mixture has cooled, 17 ml of water are added and the mixture is extracted twice with ethyl acetate. The combined extracts are dried over sodium sulfate, the solution is concentrated in vacuo and the residue is purified by chromatography on silica gel using a diethyl ether/hexane mixture (1:2% by volume) as eluent. In this way 0.4 g of α-methoxyimino-2-(o-tolyloxymethyl)phenylacetate is obtained as white crystals with the melting point 99°–100° C.

Example 2 (preparation of an intermediate)

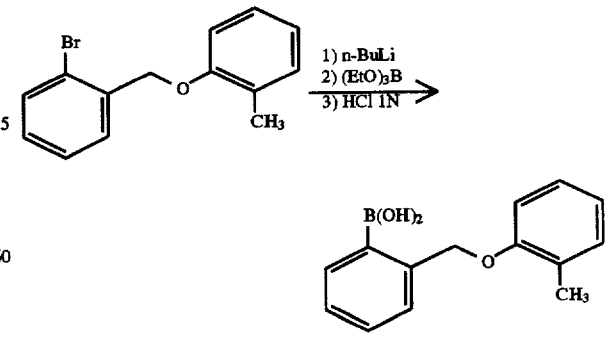

20 ml of a 1.6 molar solution of n-butyllithium in hexane are added dropwise, under a nitrogen atmosphere and with stirring, to a solution, cooled to −75° C., of 8.0 g of 1-bromo-2-(o-tolyloxymethyl)benzene in 50 ml of tetrahydrofuran at a rate such that the temperature does not exceed −70° C. After a further hour 5.4 ml of triethyl borate are added dropwise at −75° C. After stirring for 3 hours more, 5 ml of saturated ammonium chloride solution are added and the cooling bath is removed. At room temperature, 100 ml of 1N HCl solution are added and the oil which separates out is extracted twice with diethyl ether. The combined ether extracts are washed with water and dried over sodium sulfate. The white solid which remains after the solvent has been removed by distillation is purified by dissolving it in 2N aqueous sodium hydroxide solution, the solution is extracted twice with diethyl ether, and the extracts are then acidified with concentrated hydrochloric acid solution. The precipitate is filtered off and dried to give 4.1 g of 2-(o-tolyloxymethyl)benzeneboronic acid as a white powder with a melting point 170°-171° C.

Example 3: (preparation of an intermediate)

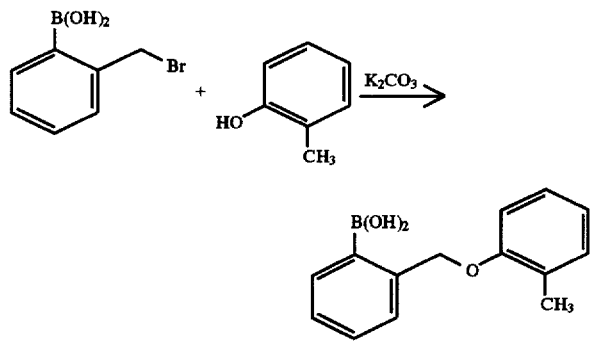

A mixture of 4.9 g of α-bromotolueneboronic acid, 2.16 g of o-cresol, 6.4 g of potassium carbonate, 0.1 g of potassium iodide, 2.5 ml of water and 25 ml of acetonitrile is stirred under reflux for 16 hours. The mixture is cooled and filtered, and the filtrate is concentrated in vacuo, acidified with 1N hydrochloric acid and extracted twice with ethyl acetate. The combined and dried extracts are concentrated in vacuo and the residue is purified by chromatography on silica gel using a 50:50% by volume mixture of diethyl ether and hexane. In this way 1 g of 2-(o-tolyloxymethyl)benzeneboronic acid is obtained whose $^1$H-NMR spectrum is identical to that of the boronic acid from Example 2.

Example 4: (preparation of an intermediate)

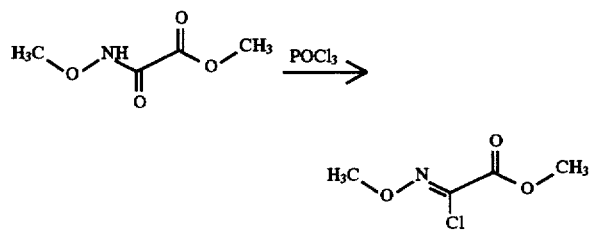

A mixture of 26.6 g of methyl N-methoxyoxamate and 0.5 g of dimethylformamide in 100 ml of phosphorus oxytrichloride is maintained under reflux for 18 hours. After the removal of the excess phosphorus oxytrichloride by distillation the residue is poured into ice-water and the yellow oil which separates out is extracted twice with diethyl ether. The combined extracts are washed with water and dried over sodium sulfate and the solvent is removed by distillation. In this way 24.6 g of methyl chloromethoxyiminoacetate are obtained as pale yellow crystals with the melting point 43°-44° C.

Methyl bromomethoxyiminoacetate (pale yellow crystals with the melting point 49°-51° C.) is prepared analogously using phosphorus oxytribromide.

Example 5: (preparation of an intermediate)

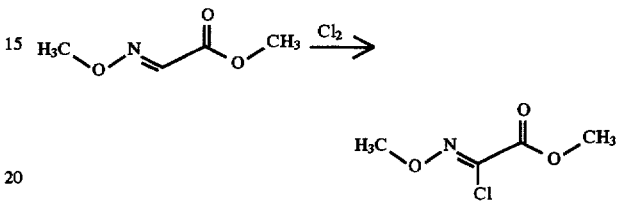

Chlorine gas is passed at a temperature of 10°-15° C. for one hour into a mixture of 2.9 g of methyl methoxyiminoacetate and 20 ml of water. The mixture is then stirred at 25°-30° C. for 5 hours and subjected to extraction with dichloromethane. The organic phase is dried over sodium sulfate. After the removal of the solvent by distillation, 2.4 g of methyl chloromethoxyiminoacetate remain as pale yellow crystals with the melting point 43°-44° C.

Example 6: Preparation of

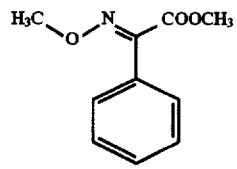

1.58 g of phenylboronic acid and 1.52 g of methyl 2-chloro-2-methoximinoacetate are dissolved in a mixture of 15 ml of toluene and 4 ml of ethanol, and 0.27 g of bis (triphenylphosphine)palladium(II) dichloride and 7.5 ml of 1 molar Na$_2$CO$_3$ solution are added with stirring, the initially yellow suspension developing a red colour. The mixture is stirred for half an hour at room temperature, then for one hour at 45° C. and a further hour at 50° C. After the mixture has been cooled to room temperature, 20 ml of water are added and the toluene phase is separated off. The aqueous phase is twice extracted with 40 ml of ethyl acetate, and the combined organic extracts are filtered over Hyflo. The filtrate is washed with 20 ml of water, dried over Na$_2$SO$_4$ and concentrated by evaporation. 1.7 g are obtained of a red-brown oil which is purified on a silica gel column using ethyl ether/hexane (1:4) as eluent. Yield: 0.65 g (43.9% of theoretical).

The oxime ethers VII can be prepared by a method analogous to that described in the aforegoing examples using a boronic acid IIb and reacting it with the methyl chloro- or bromomethoxyiminoacetate in the presence of a Pd catalyst.

TABLE 1

Intermediates of the formula IIb

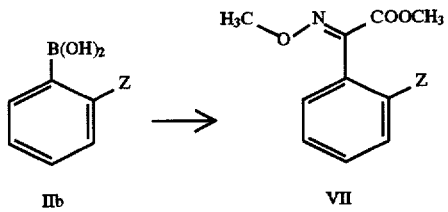

| No. | Z | Phys. data |
|---|---|---|
| 1 | 2-Tolyloxymethyl | m.p. 170–171° C. |
| 2 | Benzyl | |
| 3 | Phenethyl | |
| 4 | —CH=CH—C$_6$H$_5$ | |
| 5 | —C≡C—C$_6$H$_5$ | |
| 6 | Phenoxy | |
| 7 | Phenoxymethyl | |
| 8 | Benzyloxy | |
| 9 | 2,5-Dimethylphenoxymethyl | |

TABLE 1-continued

Intermediates of the formula IIb

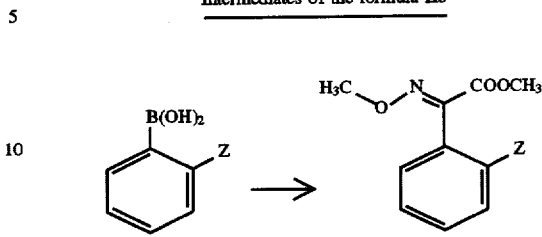

| No. | Z | Phys. data |
|---|---|---|
| 10 | 4-[6-(2-Cyanophenoxy)pyrimidinyloxy] | |

The above intermediates of the formula IIb of Table 1 are a further subject of the present invention.

TABLE 2

The oxime ethers VIII can be prepared by a method analogous to that described in Example 1 using a boronic acid IIc and reacting it with a methoxyiminoacetic ester of the formula IV in the presence of a Pd catalyst, the oxime ethers VIII being characterized by their melting point and/or MS(M$^+$(intensity in %); base peak):

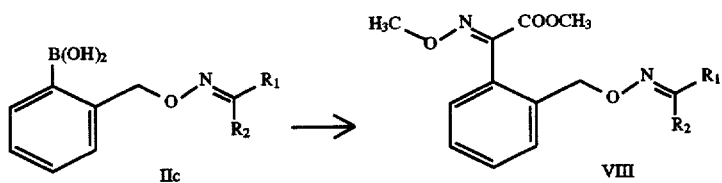

| Example | R$_2$ | R$_1$ | Phys. data |
|---|---|---|---|
| 11 | CH$_3$ | β-Naphthyl | m.p. 97–98° C. |
| 12 | CH$_3$ | α,α,α-Trifluoro-m-tolyl | 408(<0.5); 186 |
| 13 | CH$_3$ | 3,4-Dichlorophenyl | m.p. 103–105° C. |
| 14 | CH$_3$ | 2-Thienyl | 346(2); 116 |
| 15 | CH$_3$ | 2-Pyridyl | m.p. 82–84° C. |
| 16 | CH$_3$ | 3-Cyclopropylmethoxyphenyl | 410(8); 116 |
| 17 | CH$_3$ | 4-Chlorophenyl | 343(2); 116 |
| 18 | n-Propyl | Phenyl | 368(<0.5); 116 |
| 19 | CH$_3$ | 4-Methoxyphenyl | 370(10); 116 |
| 20 | CH$_3$ | 3,4,5-Trimethoxyphenyl | 430(49); 116 |
| 21 | CH$_3$ | 2-Furyl | m.p. 95–97° C. |
| 22 | CH$_3$ | 3-Bromophenyl | 389(0.5); 116 |
| 23 | CH$_3$ | 3-Cyanophenyl | m.p. 103–104° C. |
| 24 | CH$_3$ | 3-Trifluoromethylbenzyl | 422(4); 116 |
| 25 | CH$_3$ | 4-Nitrophenyl | 354(1); 116 |
| 26 | CH$_3$ | 3-Nitrophenyl | 354(0.5); 116 |
| 27 | CF$_3$ | Phenyl | 222(4); 116 |
| 28 | CH$_3$CH$_2$— | Phenyl | 323(2); 116 |
| 29 | i-Propyl | Phenyl | 368(1); 116 |
| 30 | CF$_3$ | 3-Bromophenyl | 252(2); 116 |
| 31 | CF$_3$ | 4-Tolyl | 222(6); 116 |
| 32 | CH$_3$ | 2-Benzofuryl | m.p. 110–112° C. |
| 33 | CH$_3$ | 3,5-Di(trifluoromethyl)-phenyl | m.p. 76–78° C. |
| 34 | CH$_3$ | 4-Fluorophenyl | m.p. 89–90° C. |
| 35 | CH$_3$O—CH$_2$— | β-Naphthyl | 420(4); 45 |
| 36 | Cyclopropyl | Phenyl | 355(3); 116 |
| 37 | CH$_3$ | 1-Phenoxyethyl | 291(63); 116 |
| 38 | CH$_3$ | 3,4-Methylenedioxyphenyl | 384(12); 116 |

TABLE 2-continued

The oxime ethers VIII can be prepared by a method analogous to that described in Example 1 using a boronic acid IIc and reacting it with a methoxyiminoacetic ester of the formula IV in the presence of a Pd catalyst, the oxime ethers VIII being characterized by their melting point and/or MS(M$^+$(intensity in %); base peak):

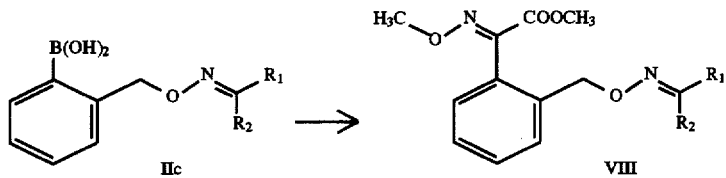

| Example | R$_2$ | R$_1$ | Phys. data |
|---|---|---|---|
| 39 | CF$_3$ | 3-Trifluoromethylphenyl | 240(3); 116 |
| 40 | CH$_3$ | 3-Fluorophenyl | m.p. 84–85° C. |
| 41 | Cyclopropyl | 3,4-Methylenedioxyphenyl | m.p. 69–72° C. |
| 42 | CH$_3$ | 4-Bromophenyl | m.p. 78° C. |
| 43 | CH$_3$ | 6-(1,4-Benzodioxanyl) | m.p. 103–106° C. |
| 44 | Cyclopropyl | 6-(1,4-Benzodioxanyl) | 424(20); 116 |
| 45 | CH$_3$ | 3,4-(Difluoromethylenedioxy)-phenyl | m.p. 88–89° C. |
| 46 | CH$_3$ | 3-Methoxyphenyl | m.p. 96–97° C. |
| 47 | CH$_3$ | 3-Propargyloxyphenyl | 394(2); 116 |
| 48 | CH$_3$ | 4-Cyanophenyl | m.p. 80–81° C. |
| 49 | CH$_3$ | 4-Methoxy-3-(methylthiomethyl)phenyl | m.p. 74–78° C. |
| 50 | CH$_3$ | ![structure] | m.p. 130–132° C. |
| 51 | CH$_3$ | ![structure] | m.p. 108–113° C. |
| 52 | CH$_3$ | Phenyl | m.p. 69–71° C. |
| 53 | CH$_3$ | 3,5-Dichlorophenyl | m.p. 90–93° C. |
| 54 | CH$_3$ | 3-Trifluoromethoxyphenyl | 425(1); 116 |
| 55 | Cyclopropyl | 4-Chlorophenyl | m.p. 78–84° C. |
| 56 | Cyclopropyl | 3-Chlorophenyl | 400(2); 116 |
| 57 | Cyclopropyl | 4-Fluorophenyl | m.p. 64–65° C. |
| 58 | Cyclopropyl | 3-Fluoro-4-methoxyphenyl | 414(17); 116 |
| 59 | Cyclopropyl | 3-Trifluoromethylphenyl | 434(2); 116 |
| 60 | Cyclopropyl | 4-Bromophenyl | m.p. 93° C. |
| 61 | CH$_3$ | 3-Chlorophenyl | m.p. 79–81° C. |
| 62 | CH$_3$ | 3-Allyloxyphenyl | m.p. 54–55° C. |
| 63 | CH$_3$S | 3,4-Methylenedioxyphenyl | 416(53); 116 |
| 64 | CH$_3$ | 2-Chlorophenyl | 343(3): M-OCH$_3$; 116 |
| 65 | CH$_3$ | 3-(Chlorodifluoromethoxy)-phenyl | 440(<1); 116 |
| 66 | CH$_3$ | 3-Tolyl | m.p. 99–101° C. |
| 67 | CH$_3$ | 4-Methoxy-2,3,5,6-tetrafluorophenyl | m.p. 88–91° C. |
| 68 | CH$_3$ | 4-Methylthio-2,3,5,6-tetrafluorophenyl | m.p. 84–87° C. |
| 69 | CH$_3$CH$_2$ | 3,4-Difluoromethylenedioxyphenyl | m.p. 52–55° C. |
| 70 | CH$_3$ | 2-(6-Chlorothienyl) | 382(10); 116 |
| 71 | n-Propyl | 3,4-Difluoromethylenedioxyphenyl | m.p. 102–105° C. |
| 72 | CH$_3$ | 4-Ethoxy-3-methoxyphenyl | m.p. 110–111° C. |
| 73 | H | Phenyl | m.p. 82–83° C. |
| 74 | H | 4-Chlorophenyl | m.p. 158–159° C. |
| 75 | CH$_3$S | Phenyl | 372(4); 116 |
| 76 | CH$_3$O | Phenyl | 356(2.5); 116 |
| 77 | CH$_3$ | 4-Cyclopropylmethoxyphenyl | m.p. 98–99° C. |
| 78 | CH$_3$CH$_2$ | 3-Nitrophenyl | m.p. 95–96° C. |
| 79 | CH$_3$O | 4-Chlorophenyl | 390(2); 116 |
| 80 | CH$_3$S | 4-Chlorophenyl | 406(2); 116 |
| 81 | CH$_3$S | 3-Trifluoromethylphenyl | 440(1); 116 |

TABLE 2-continued

The oxime ethers VIII can be prepared by a method analogous to that described in Example 1 using a boronic acid IIc and reacting it with a methoxyiminoacetic ester of the formula IV in the presence of a Pd catalyst, the oxime ethers VIII being characterized by their melting point and/or MS(M⁺(intensity in %); base peak):

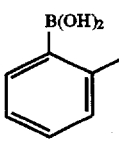

| Example | R₂ | R₁ | Phys. data |
|---|---|---|---|
| 82 | CH₃O | 3-Trifluoromethylphenyl | 424(0.6); 116 |
| 83 | CH₃ | 4-Fluoro-3-trifluoromethyl-phenyl | m.p. 60–63° C. |
| 84 | CH₃ | 4-Difluoromethoxyphenyl | m.p. 82–83° C. |
| 85 | CH₃CH₂ | 2-Thienyl | m.p. 80–84° C. |
| 86 | CH₃ | 6-Methoxy-2-naphthyl | m.p. 118–119° C. |
| 87 | CH₃ | 4-Trifluoromethylphenyl | m.p. 71° C. |
| 88 | CH₃ | 3,4-Propylenedioxyphenyl | m.p. 97–100° C. |
| 89 | CH₃ | 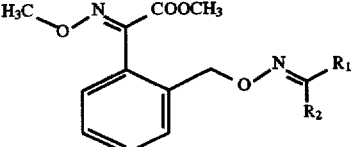 | m.p. 103–104° C. |
| 90 | CH₃ | 3-Difluoromethoxyphenyl | m.p. 68–69° C. |
| 91 | | 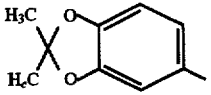 | m.p. 108–110° C. |
| 92 | | 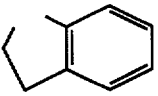 | m.p. 92–94° C. |
| 93 | | 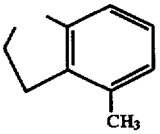 | m.p. 108–110° C. |
| 94 | | 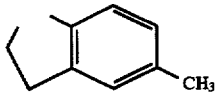 | m.p. 98–101° C. |
| 95 | | 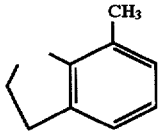 | m.p. 89–92° C. |
| 96 | | 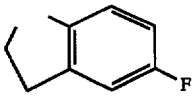 | m.p. 124–127° C. |
| 97 | | 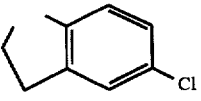 | m.p. 82–86° C. |

TABLE 2-continued

The oxime ethers VIII can be prepared by a method analogous to that described in Example 1 using a boronic acid IIc and reacting it with a methoxyiminoacetic ester of the formula IV in the presence of a Pd catalyst, the oxime ethers VIII being characterized by their melting point and/or MS(M⁺(intensity in %); base peak):

IIc → VIII

| Example | R₂ | R₁ | Phys. data |
|---|---|---|---|
| 98 | | (benzocycloheptane fused ring) | m.p. 118–120° C. |
| 99 | | (benzofuran-type fused ring with O) | m.p. 97–104° C. |
| 100 | | (fused O-containing ring with F on phenyl) | 386(13); 116 |

The above intermediates in the formula IIc of Table 2 are a further subject of the present invention, especially those in which R₁ is phenyl having from 0 to 3 substituents and
R₂ is attentively methyl, ethyl, trifluoromethyl, cyclopropyl, methoxy or methylthio.

What is claimed is:

1. A process for the preparation of a compound of formula I

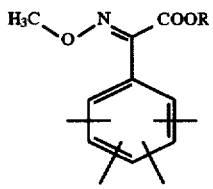

I wherein one CH group of the aromatic ring may be replaced by N (forming pyridyl) and wherein two of the four substitutable valencies of the ring, may in adjacent position represent a fused-on, unsubstituted or substituted five- or six-membered ring which may contain one to three identical or different heteroatoms selected from N, S and O, and in which R is C₁–C₁₂alkyl, comprising reacting, A) by reaction of boronic acid represented by structural formula II

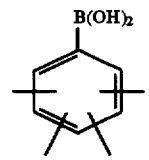

II or of the trimeric form III

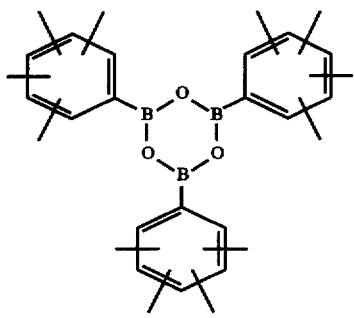

III which is in equilibrium with II, in the presence of a palladium catalyst, with a methoxyiminoacetic ester represented by structural formula IV

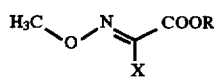

IV wherein R is C₁–C₁₂alkyl, and
X is a leaving group, or

B) by reaction of a methoxyiminoacetic ester of the formula Xa or Xb

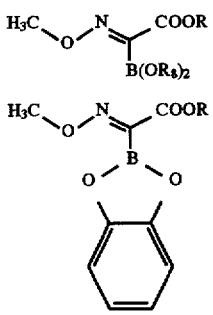

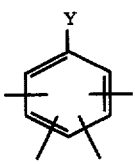

wherein R and R$_8$ are each C$_1$–C$_{12}$alkyl in the presence of a palladium catalyst, with a halophenyl compound represented by the structural formula XI

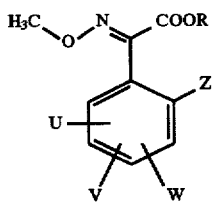

which is substituted as desired and in which

Y is Br or I and wherein two of the four substitutable valencies of the ring, may in adjacent position represent a fused-on, unsubstituted or substituted five- or six-membered ring which may contain one to three identical or different heteroatoms selected from N, S and O.

2. A process according to claim 1 for the preparation of a compound of the formula Ia

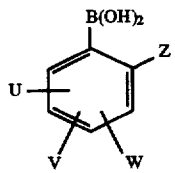

wherein said boronic acid is represented by the structure IIa

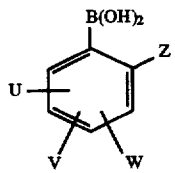

in which

R is C$_1$–C$_{12}$alkyl and

U, V, W and Z are defined as below:

Z is halogen, nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted heteroarylalkyl, unsubstituted or substituted heteroaryloxyalkyl, unsubstituted or substituted heteroarylthioalkyl, unsubstituted or substituted alkenyl, unsubstituted or substituted thioalkenyl, unsubstituted or substituted arylalkenyl, unsubstituted or substituted heteroarylalkenyl, unsubstituted or substituted heteroaryloxyalkenyl, unsubstituted or substituted heteroarylthioalkenyl, unsubstituted or substituted alkynyl, unsubstituted or substituted arylalkynyl, unsubstituted or substituted heteroarylalkynyl, unsubstituted or substituted aryl, unsubstituted or substituted heteroaryl, unsubstituted or substituted arylazo, unsubstituted or substituted acylamino, —OR$_{12}$, —SR$_{13}$, —SOR$_{14}$, —SO$_2$R$_{15}$, —COOR$_{16}$, —CONR$_{17}$R$_{18}$, —COR$_{19}$, —CR$_{20}$=NR$_{21}$, —N=CR$_{22}$R$_{23}$, —CR$_{24}$=N—OR$_{25}$, —CR$_{25}$R$_{26}$—O—N=C—R$_{27}$R$_{28}$, —CH$_2$—OCOR$_{39}$, or —NR$_{37}$R$_{38}$, in which the groups R$_1$ to R$_{28}$ and R$_{38}$ and R$_{39}$ are identical or different and are hydrogen, unsubstituted or substituted C$_1$–C$_6$alkyl, unsubstituted or substituted C$_1$–C$_6$alkenyl, unsubstituted or substituted C$_1$–C$_6$alkynyl, unsubstituted or substituted C$_3$–C$_6$cycloalkyl, unsubstituted or substituted cycloalkylalkyl, unsubstituted or substituted aryl, unsubstituted or substituted heteroaryl, unsubstituted or substituted aralkyl, unsubstituted or substituted heteroaralkyl, unsubstituted or substituted aryloxyalkyl, unsubstituted or substituted arylthioalkyl, unsubstituted or substituted heteroarylthioalkyl, and R$_{37}$ is hydrogen or C$_1$–C$_4$alkyl, and in which U, V and W are identical or different and are hydrogen or have one of the definitions specified for Z, or in which two of the groups, Z, U, V and W in adjacent positions of the phenyl ring, together with the carbon atoms in these positions, form an unsubstituted or substituted five- or six-membered aromatic or cycloaliphatic ring which is fused onto the aryl ring and which may or may not contain one to three heteroatoms (N, S, O).

3. A process according to claim 1, in which the Pd catalyst is selected from Pd$^{(II)}$(OAc)$_2$, (Ø$_3$P)$_2$Pd$^{(II)}$(OAc)$_2$, (Ø$_3$P)$_2$Pd$^{(II)}$Cl$_2$, (Ø$_3$P)$_4$Pd$^{(O)}$, bis[1,2-bis(diphenylphosphino)ethane]palladium$^{(O)}$, dichloro[1,1'-bis(diphenylphosphino)ferrocene]palladium$^{(II)}$, dichloro[1,3-bis(diphenylphosphino)propane]Pd$^{(II)}$, dichloro[1,4-bis(diphenylphosphino)butane]Pd$^{(II)}$, dichloro[1,2-bis(diphenylphosphino)ethane]Pd$^{(II)}$ and dichlorobis(triphenylphosphine)Pd$^{(II)}$.

4. A process according to claim 3 in which the Pd catalyst is tetrakis(triphenylphosphine)Pd$^{(O)}$.

5. A process according to claim 1, in which the leaving group is a halogen or a sulfonate.

6. A process according to claim 1, which is carried out in the presence of a solvent or solvent mixture.

7. A process according to claim 1, in which the reaction is carried out in the presence of a base.

8. A process according to claim 7, in which the base is an amine.

9. A process according to claim 7, in which the base is Na carbonate or K carbonate or Na hydrogen carbonate or K hydrogen carbonate.

10. A process according to claim 6, in which the reaction is carried out at a temperature of from 0° C. to the boiling point of the solvent.

11. A process according to claim 2, in which

Z is A—R$_1$ and

—A— adjacent to the aryl group is oxygen or a group —C≡C—, —CR$_{30}$=CR$_{31}$—, —CHR$_{31}$—CHR$_{30}$—, —CHR$_{31}$O—, —OCHR$_{31}$—, —CO—O—, —CONR$_{30}$—, —CHR$_{31}$S—, —CR$_{31}$=N—, —CHR$_{31}$—OCO—, —CHR$_{31}$ON=CR$_{30}$—, —CR$_{31}$=N—O—, —N=CR$_{30}$—, —N=N— or —CHR$_{30}$— and R$_1$ is unsubstituted or substituted alkyl, unsubstituted or substituted alkenyl, unsubstituted or substituted alkynyl, unsubstituted or substituted aralkyl, unsubstituted or substituted heteroarylalkyl, unsubstituted or substituted aryloxyalkyl, unsubstituted or substituted heteroaryloxyalkyl or heteroarylthioalkyl or unsubstituted or substituted aryl or unsubstituted or substituted heteroaryl, and $R_{30}$ and $R_{31}$ are identical or different and are straight-chain or branched $C_1$–$C_4$alkyl or hydrogen.

12. A process according to claim 11, in which

—A— is the group —O—, —CH$_2$O—, —O—CH$_2$—, —CH$_2$ON=CR$_2$—, —CH$_2$, —CH$_2$CH$_2$—, —CH=CH— or —C≡C— and $R_1$ is unsubstituted or substituted aryl or unsubstituted or substituted heteroaryl, and $R_2$ is hydrogen, $C_1$–$C_4$alkyl, $C_3$–$C_6$cycloalkyl, $CF_3$, $C_1$–$C_4$alkoxy, $C_1$–$C_4$alkylthio or $C_1$–$C_4$alkoxy-$C_1$–$C_2$alkyl, or $R_1$ and $R_2$, together with the carbon atom to which they are attached, form an unsubstituted or substituted four- to seven-membered carbocyclic ring which may or may not contain an oxygen or sulfur atom and which may also have an unsubstituted or substituted fused-on benzene ring.

13. A boronic acid of the formula IIb

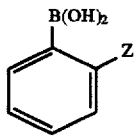

IIb in which

Z is 2-tolyloxymethyl, phenethyl, —C≡C—C$_6$H$_5$, phenoxymethyl, benzyloxy, 2,5-dimethylphenoxymethyl or 4-[6-(2-cyanophenoxy)pyrimidinyloxy].

14. A boronic acid of the formula IIc

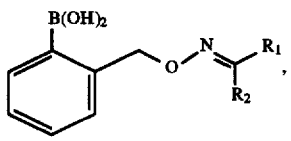

in which $R_1$ is phenyl having from 0 to 3 substituents and $R_2$ is $CH_3$, $C_2H_5$, $CF_3$, cyclopropyl, $CH_3O$ or $CH_3S$.

15. The process of claim 2 wherein said boronic acid represented by the structure IIa is an intermediate for the preparation of a compound represented by the structure Ia.

16. The process of claim 2 wherein said boronic acid is represented by the structure

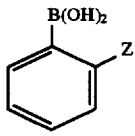

IIb wherein,

Z is 2-tolyloxymethyl, phenethyl, phenoxymethyl, benzyloxy, 2,5-dimethylphenoxy, methyl, or 4-[6-2-cyanophenoxy)pyrimidinyloxy], is an intermediate for the preparation of a compound represented by the structure:

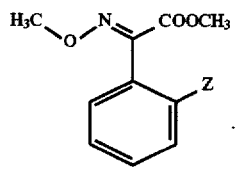

VII

17. The process of claim 2 wherein said boronic acid represented by the structure

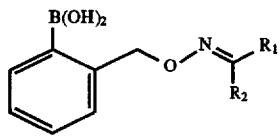

wherein, $R_1$ is phenyl, and, $R_2$ is $CH_3$, $C_2H_5$, $CF_3$, cyclopropyl, $CH_3O$ or $CH_3S$, is an intermediate for the preparation of a compound represented by the structure

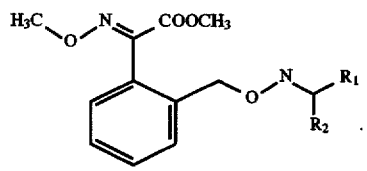

VIII

18. A methoxyiminoacetic ester represented by a structure selected from the group consisting of

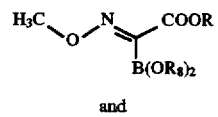

and

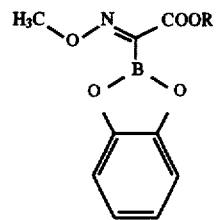

wherein R and $R_8$ are each $C_1$–$C_{12}$alkyl.

* * * * *